United States Patent
Schultz et al.

(10) Patent No.: US 9,550,183 B2
(45) Date of Patent: Jan. 24, 2017

(54) FLUIDICS SYSTEM FOR SEQUENTIAL DELIVERY OF REAGENTS

(71) Applicant: LIFE TECHNOLOGIES CORPORATION, Carlsbad, CA (US)

(72) Inventors: Jonathan Schultz, Oxford, MA (US); David Marran, Durham, CT (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 188 days.

(21) Appl. No.: 14/291,372

(22) Filed: May 30, 2014

(65) Prior Publication Data

US 2014/0271402 A1    Sep. 18, 2014

Related U.S. Application Data

(63) Continuation of application No. 13/245,649, filed on Sep. 26, 2011, now Pat. No. 8,846,378, which is a (Continued)

(51) Int. Cl.
*C12M 1/00* (2006.01)
*C12M 3/00* (2006.01)
(Continued)

(52) U.S. Cl.
CPC ............ *B01L 3/502* (2013.01); *B01L 3/50273* (2013.01); *B01L 3/502715* (2013.01);
(Continued)

(58) Field of Classification Search
None
See application file for complete search history.

(56) References Cited

U.S. PATENT DOCUMENTS

| | | |
|---|---|---|
| 3,531,258 A | 9/1970 | Merrifield |
| 4,008,736 A | 2/1977 | Wittmann-Liebold et al. |

(Continued)

FOREIGN PATENT DOCUMENTS

| | | |
|---|---|---|
| CN | 1472526 | 2/2004 |
| CN | 2831115 | 10/2006 |

(Continued)

OTHER PUBLICATIONS

Anderson, E. et al., "A system for multiplexed direct electrical detection of DNA synthesis", *Sensors and Actuators B Chem.*, vol. 129, 2008, pp. 79-86.

(Continued)

*Primary Examiner* — Joseph G Dauner

(57) ABSTRACT

The invention provides a passive fluidics circuit for directing different fluids to a common volume, such as a reaction chamber or flow cell, without intermixing or cross contamination. The direction and rate of flow through junctions, nodes and passages of the fluidics circuit are controlled by the states of upstream valves (e.g. opened or closed), differential fluid pressures at circuit inlets or upstream reservoirs, flow path resistances, and the like. Free diffusion or leakage of fluids from unselected inlets into the common outlet or other inlets at junctions or nodes is prevented by the flow of the selected inlet fluid, a portion of which sweeps by the inlets of unselected fluids and exits the fluidics circuit by waste ports, thereby creating a barrier against undesired intermixing with the outlet flow through leakage or diffusion. The invention is particularly advantageous in apparatus for performing sensitive multistep reactions, such as pH-based DNA sequencing reactions.

10 Claims, 10 Drawing Sheets

Related U.S. Application Data continuation of application No. 12/785,667, filed on May 24, 2010, now Pat. No. 8,546,128, and a continuation-in-part of application No. 12/474,897, filed on May 29, 2009, now abandoned, and a continuation-in-part of application No. 12/475,311, filed on May 29, 2009, now abandoned.

(60) Provisional application No. 61/291,627, filed on Dec. 31, 2009, provisional application No. 61/205,626, filed on Jan. 22, 2009, provisional application No. 61/198,222, filed on Nov. 4, 2008, provisional application No. 61/196,953, filed on Oct. 22, 2008.

(51) Int. Cl.
  *C12M 1/34* (2006.01)
  *B01L 3/00* (2006.01)
  *C12Q 1/68* (2006.01)
  *G01N 27/447* (2006.01)
  *G01N 35/10* (2006.01)

(52) U.S. Cl.
  CPC ... *B01L 3/502738* (2013.01); *B01L 3/502776* (2013.01); *B01L 3/52* (2013.01); *C12Q 1/6869* (2013.01); *G01N 27/447* (2013.01); *B01J 2219/00389* (2013.01); *B01J 2219/00394* (2013.01); *B01L 3/502769* (2013.01); *B01L 2300/0636* (2013.01); *B01L 2300/0645* (2013.01); *B01L 2300/0861* (2013.01); *B01L 2300/0864* (2013.01); *B01L 2300/0874* (2013.01); *B01L 2300/0877* (2013.01); *B01L 2400/0487* (2013.01); *G01N 35/1002* (2013.01); *G01N 35/1097* (2013.01); *Y10T 137/0318* (2015.04); *Y10T 137/0424* (2015.04); *Y10T 137/85938* (2015.04)

(56) References Cited

U.S. PATENT DOCUMENTS

| | | | |
|---|---|---|---|
| 4,558,845 | A | 12/1985 | Hunkapiller |
| 4,722,830 | A | 2/1988 | Urie et al. |
| 5,082,788 | A | 1/1992 | Farnsworth et al. |
| 5,126,022 | A | 6/1992 | Soane et al. |
| 5,132,418 | A | 7/1992 | Caruthers et al. |
| 5,284,566 | A | 2/1994 | Cuomo et al. |
| 5,313,984 | A | 5/1994 | Garwood, Jr. et al. |
| 5,498,392 | A | 3/1996 | Wilding et al. |
| 5,587,128 | A | 12/1996 | Wilding et al. |
| 6,001,299 | A | 12/1999 | Kawabe et al. |
| 6,010,607 | A | 1/2000 | Ramsey |
| 6,033,546 | A | 3/2000 | Ramsey |
| 6,054,034 | A | 4/2000 | Soane et al. |
| 6,399,952 | B1 | 6/2002 | Maher et al. |
| 6,499,499 | B2 | 12/2002 | Dantsker et al. |
| 6,613,525 | B2 | 9/2003 | Nelson et al. |
| 6,960,437 | B2 | 11/2005 | Enzelberger et al. |
| 7,223,371 | B2 | 5/2007 | Hayenga et al. |
| 2002/0076825 | A1 | 6/2002 | Cheng et al. |
| 2003/0175990 | A1 | 9/2003 | Hayenga et al. |
| 2004/0072278 | A1 | 4/2004 | Chou et al. |
| 2004/0096368 | A1 | 5/2004 | Davis et al. |
| 2004/0146849 | A1 | 7/2004 | Huang et al. |
| 2004/0224380 | A1 | 11/2004 | Chou et al. |
| 2005/0100939 | A1 | 5/2005 | Namsaraev et al. |
| 2005/0202504 | A1 | 9/2005 | Anderson et al. |
| 2006/0093488 | A1 | 5/2006 | Wong et al. |
| 2006/0182664 | A1 | 8/2006 | Peck et al. |
| 2007/0117099 | A1 | 5/2007 | Engelhardt et al. |
| 2007/0217963 | A1 | 9/2007 | Elizarov et al. |
| 2008/0032295 | A1 | 2/2008 | Toumazou et al. |
| 2009/0026082 | A1 | 1/2009 | Rothberg et al. |
| 2009/0127589 | A1 | 5/2009 | Rothberg et al. |
| 2010/0137143 | A1 | 6/2010 | Rothberg et al. |
| 2012/0143531 | A1* | 6/2012 | Davey ............ G01N 33/48785 702/51 |

FOREIGN PATENT DOCUMENTS

| | | |
|---|---|---|
| JP | 2005-519751 | 7/2005 |
| JP | 2006524797 | 11/2006 |
| JP | 2011-527012 | 10/2011 |
| WO | 98/49548 | 11/1998 |
| WO | 99/19717 | 4/1999 |
| WO | 02/24322 | 3/2002 |
| WO | 2005/016536 | 2/2005 |
| WO | 2007/106579 | 9/2007 |
| WO | 2009/119698 | 10/2009 |
| WO | 2010/138186 | 12/2010 |

OTHER PUBLICATIONS

Brenner, et al., "Gene expression analysis by massively parallel signature sequencing (MPSS) on microbead arrays", *Nature Biotechnology*, vol. 18, No. 6, Jun. 2000, pp. 630-634.

Marguiles, et al., "Genome Sequencing in Microfabricated High-Density Picolitre Reactors", *Nature*, vol. 437, No. 7057, 2005, pp. 376-380.

International Search Report and Written Opinion for International Application No. PCT/US10/01547 mailed Aug. 5, 2010, 12 pages.

International Preliminary Report on Patentability for International Application No. PCT/US2010/01547 mailed Nov. 29, 2011, 8 pages.

Pourmand, N. et al., "Direct electrical detection of DNA synthesis", *PNAS*, vol. 103(17), 2006, pp. 6466-6470.

Ronaghi, M. et al., "A Sequencing Method Based on Real-Time Pyrophosphate", *Science*, vol. 281, 1998, 363-365.

Sia, S. et al., "Microfluidic devices fabricated in poly(dimethylsiloxane) for biological studies", *Electrophoresis*, 24:, 2003, pp. 3563-3576.

Unger, M. et al., "Monolithic Microfabricated Valves and Pumps by Multilayer Soft Lithography", *Science*, 288:, 2000, pp. 113-116.

European Search Report for European Application No. EP10780933 mailed Jun. 26, 2015, 2 pages.

* cited by examiner

FLUIDICS SYSTEM FOR SEQUENTIAL DELIVERY OF REAGENTS

This is a continuation of U.S. patent application Ser. No. 13/245,649, filed 26 Sep. 2011, which is a continuation of U.S. patent application Ser. No. 12/785,667, filed 24 May 2010, now U.S. Pat. No. 8,546,128, which is a continuation-in-part of U.S. patent application Ser. No. 12/474,897 (which claims priority under U.S. provisional application Ser. No. 61/205,626, filed Jan. 22, 2009; 61/198,222, filed Nov. 4, 2008; and, 61/196,953, filed Oct. 22, 2008) and Ser. No. 12/475,311, both filed 29 May 2009, and claims priority under U.S. provisional application Ser. No. 61/291,627 filed 31 Dec. 2009. Each of the foregoing applications is incorporated by reference in their entireties.

BACKGROUND

Many applications require the regulation of multiple fluid flows in a manner that minimizes intermixing or cross-contamination of the different fluids. Such applications include multi-step synthetic or analytical processes that are carried out in a common volume and that comprise successive cycles of reagent delivery using fluids from separate reservoirs. e.g. Margulies et al. Nature, 437: 376-380 (2005); Merrifield et al, U.S. Pat. No. 3,531,258; Caruthers et al, U.S. Pat. No. 5,132,418; Rothberg et al, U.S. patent publication 2009/0127589, and the like. Although fluidics systems are available for selectively switching multiple reagent solutions to a common chamber for processing, they suffer from several deficiencies, including but not limited to, the presence of large surface areas that can adsorb or retain reagents, large physical size which makes it difficult to use with miniaturized fluidics components, e.g. see Rothberg et al (cited above), less accessible surfaces including edges and/or corners which make complete purging and removal of successive reagents difficult or inefficient, and the use of moving parts which can wear out and lead to higher manufacturing and assembly costs, e.g. Hunkapiller, U.S. Pat. No. 4,558,845; Wittmann-Liebold et al, U.S. Pat. No. 4,008,736; Farnsworth et al, U.S. Pat. No. 5,082,788; Garwood et al, U.S. Pat. No. 5,313,984; or the like.

In view of the above, it would be advantageous to have available a device for regulating multiple fluid flows to a common volume for complex synthetic or analytical processes which overcame the deficiencies of current approaches.

SUMMARY OF THE INVENTION

The present invention is directed to apparatus and methods for delivering multiple fluids to a common volume, such as for example, a passage or conduit to a reaction chamber or flow cell. The invention also includes applications of such apparatus and methods in multistep analytical or synthetic processes. The present invention is exemplified in a number of implementations and applications, some of which are summarized below and throughout the specification.

In one aspect, the invention provides a passive fluidics circuit for sequentially directing different fluids to a common volume, such as a reaction chamber or flow cell, without intermixing or cross contamination. As used herein, such sequential directing is sometimes referred to as "multiplexing" a plurality of fluid flows. The direction and rate of flow through junctions, nodes and passages of the fluidics circuit are controlled by the states of upstream valves (e.g. opened or closed), differential fluid pressures at circuit inlets or upstream reservoirs, flow path resistances, and the like. Free diffusion or leakage of fluids from unselected inlets into the common outlet or other inlets at junctions or nodes is prevented by the flow of the selected inlet fluid, a portion of which sweeps by the inlets of unselected fluids and exits the fluidics circuit by way of waste ports, thereby creating a barrier against undesired intermixing with the outlet flow through leakage or diffusion. In one aspect, the selected fluidic inlet provides a laminar flow of fluid through the fluidics node.

In another aspect, the invention provides a fluidics circuit for controlling a plurality of fluid flows, the fluidics circuit comprising: (a) a fluidics node having an outlet and a plurality of fluid inlets; and (b) at least one waste port in fluid communication with the fluidics node by one or more passages each having a fluid resistance, the fluid resistances of the passages being selected so that whenever a fluid flows solely through a single fluid inlet to form a flow in the fluidics node a portion of such fluid exits the fluidics node through the outlet and the remainder of such fluid exits the fluidics node through the one or more passages, such that any fluid entering the fluidics node from inlets without fluid flows (i.e. "unselected inlets") is directed through the one or more passages to the one or more waste ports. In one embodiment, the plurality of fluid flows is controlled to provide a predetermined sequence of fluid flows through the outlet of the fluidics node. In another embodiment, such control is implemented by valves and differential pressures applied to the fluids of the flows upstream of the fluidics circuit.

In another aspect, the invention provides a fluidics circuit with no moving parts that sequentially directs multiple fluids to a common volume with no intermixing. Since the fluidics circuit comprises only a node and a plurality interconnected passages where fluid movement is controlled by remotely positioned valves, pumps, it can be readily miniaturized by conventional microfluidics techniques for applications where size and mass are critical factors. Furthermore, the use of the fluidics circuit for fluid switching without the use of impermeable barriers makes the circuit ideal for use in processes where a stable reference potential is required, such as in electrochemical processes.

DETAILED DESCRIPTION

Figure 1A:
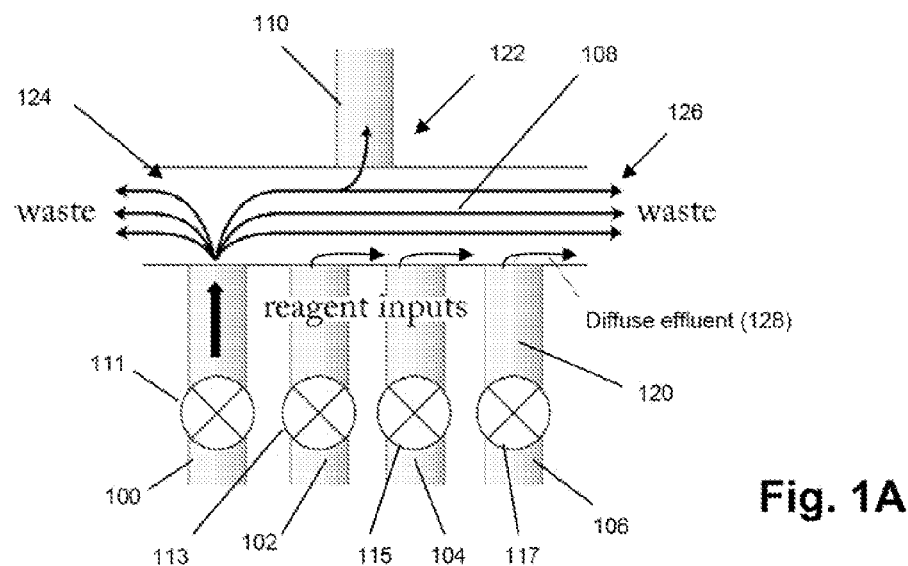
FIG. 1A is an illustration of one embodiment of the invention which has inlets and an outlet on opposing surfaces of a fluidics node.

The practice of the present invention may employ, unless otherwise indicated, conventional techniques and descriptions of mechanical engineering, electronics, fluid mechanics, and materials science, which are within the skill of the art. Such conventional techniques include, but are not limited to, design and fabrication of fluidics and microfluidics devices, and the like. Specific illustrations of suitable techniques can be had by reference to the example herein below. However, other equivalent conventional procedures can, of course, also be used.

The invention provides methods and apparatus for rapidly and cleanly switching flows of different fluids to a common outlet using a fluidics circuit. In one aspect, the fluidics circuit of the invention is combined with fluidic reservoirs, valves, pressure sources, pumps, control systems, and/or like components, to form a fluidics system for delivering separate fluid flows having predetermined rates and durations to a common volume, such as an outlet, chamber, flow cell, or the like. Such fluidics circuits are particularly useful in fluidics systems in apparatus for carrying out multi-step chemical, enzymatic, or electrochemical processes, such as described Margulies et al, Nature, 437: 376-380 (2005); Merrifield et al. U.S. Pat. No. 3,531,258; Brenner et al, Nature Biotechnology, 18: 630-634 (2000); Ronaghi et al, Science, 281: 363-365 (1998); Caruthers et al, U.S. Pat. No. 5,132,418; Namsaraev et al, U.S. patent publication 2005/0100939; Rothberg et al, U.S. patent publication 2009/0127589; and the like.

In one aspect, the fluidics circuit of the invention provides a junction where a flow of a selected fluid is split into at least two branches: one branch is directed to an outlet and from there to a flow cell or reaction chamber for use and the other branch is directed past the unselected fluid inlets and from there away from the outlet and to a waste port. In one embodiment, such flows are created by balancing the fluid resistance of the fluid outlet and that of the one or more passages between the fluid inlets and the waste port. Preferably, the flow rates, fluid viscosities, compositions, and geometries and sizes of the passages, chambers and nodes are selected so that fluid flow is laminar within the fluidics circuit. Guidance for making such design choices is readily available from conventional treatises on fluid dynamics, e.g. Acheson, Elementary Fluid Dynamics (Clarendon Press, 1990), and from free or commercially available software for modeling fluidics systems, e.g. SolidWorks from Dassault Systems (Concord. Mass.); Flowmaster from Flow Master USA, Inc. (Glenview, Ill.); and Open FOAM (open source code for computational fluid dynamics available on the world wide web, www.openefd.co.uk). Fluidic circuits and apparatus of the invention are particularly well suited for meso-scale and micro-scale fluidics systems, for example, fluidics systems having passage cross-sections in the range of tens of square microns to a few square millimeters, or having flow rates in the range of from a few nL/sec to a hundreds of µL/sec. The number of fluid flows controlled by fluidics circuits of the invention can vary widely. In one aspect, fluidics circuits of the invention control a plurality of flows in the range of from 2 to 12 different fluids, or in another aspect in the range of from 2 to 6 different fluids.

Fluidics Circuits

Figure 1B:
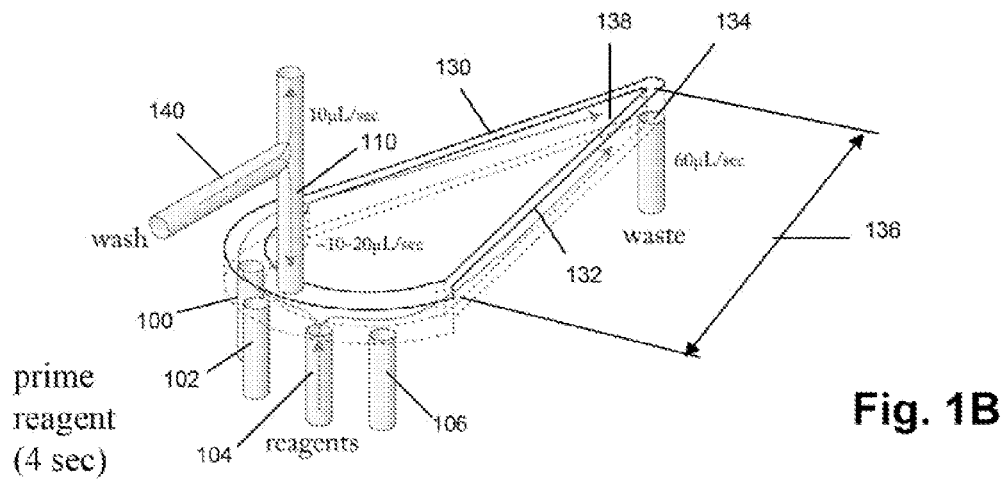
FIGS. 1B-1D illustrate priming, reagent flow, and wash steps in an embodiment of the invention.
Figure 1C:
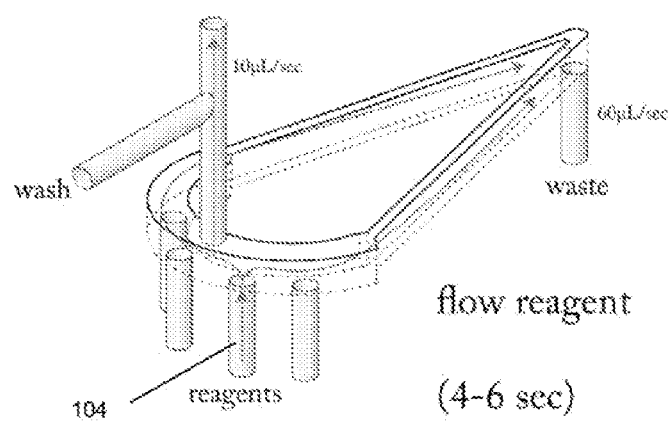
Figure 1D:
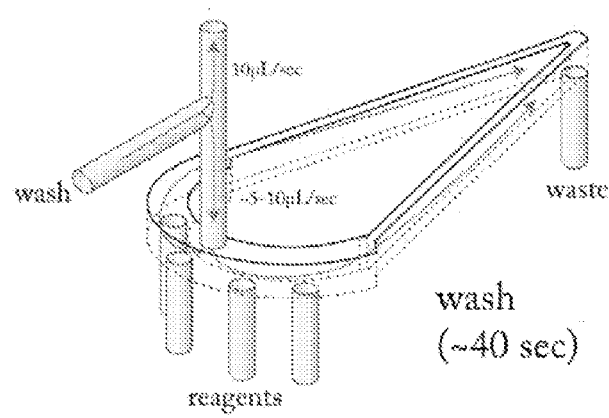

The design and operation of one embodiment of the invention is partially illustrated in FIG. 1A. Four fluid inlets, or reagent inputs, (100, 102, 104, 106) are connected to fluidics node (108) and are in fluid communication with, and on an opposing surface to outlet (110). Valve (111) is shown open so that fluid passes through inlet (100) into fluidics node (108). A portion (124) of the fluid travels through a passage shown on the left, a portion (126) travels through a passage shown on the right, and a portion exits the fluidics node through outlet (110). Preferably the three fluid flows are laminar and the flow along the surface containing the fluid inlets exits the fluidic node in a period of time that is much less than the time it would take material from the unselected inlets (diffuse effluent (128)) to diffuse to the opposing surface of the fluidics node. In this way, intermixing of the different input reagents that exit through outlet (110) is avoided. In one mode of operation, reagent inputs are selected by opening the valve corresponding to such reagent and closing all the other valves. As illustrated in this embodiment, valve (111) is open and valves (113, 115, and 117) are closed. In the closed state, even though there is no flow in the unselected inlets, a volume (for example, 120) of the unselected fluid is in free diffusive contact with the selected fluid. The split laminar flow of the selected fluid to both outlet (110) and past the unselected inlets and to the waste ports prevents undesired mixing. FIGS. 1B-1D further illustrate the operation of the above embodiment. As in FIG. 1A, inlets (100, 102, 104, and 106) connect to fluidics node (108) on a surface opposite of outlet (110) and passages (130 and 132) connect fluidics node (108) to waste port (134). The length (136) and width (138) of passages (130 and 132) are selected to provide fluid resistance so that the flow of fluid from an inlet is balanced between fluid exiting the node through outlet (110) and fluid exiting the node through passages (130 and 132). Also illustrated is wash fluid inlet (140) which is connected to outlet (110) and in fluid communication with fluidics node (110). In one mode of operation, referred to as "prime reagent" mode, wash inlet valve (not shown) is opened and valve (not shown) of reagent inlet (104) is opened. A wash solution flows into outlet (110) and towards an application, e.g. a flow cell containing a chip, as described in Rothberg et al (cited above), and towards fluidics node (108) where it combines with and constrains fluid from inlet (104) to flow into waste port (134). Exemplary flow rates and times are listed in the figure for a particular application described more fully below, but generally such rates and time are design choices that depend on a particular application. In another mode of operation, referred to in FIG. 1C as "flow reagent" mode, the flow of wash solution is shut off and the sole flow emanates from inlet (104). The flow is split into three branches two traveling through passages (130) and (132) and one traveling through outlet (110). In another mode of operation, referred to in FIG. 1D as "wash" mode valves of all fluid inlets (100, 102, 104 106) are close and the valve of wash inlet (140) is opened so that only wash solution enters the fluidics node (108), passes over inlets (100, 102, 104, 106), and exits through passages (130) and (132).

Figure 2:
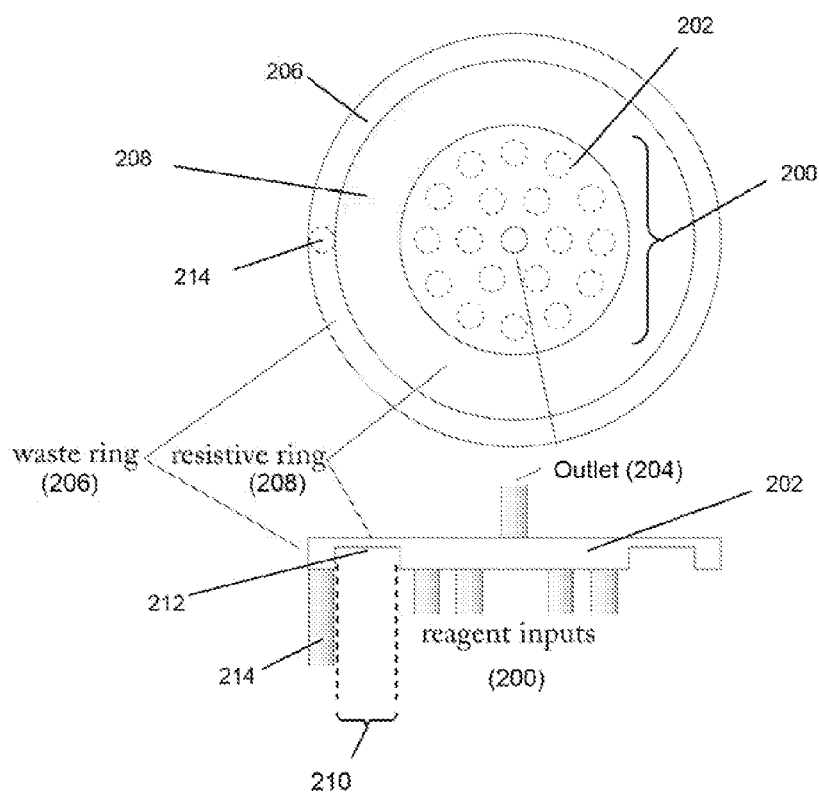
FIG. 2 illustrates another embodiment of the invention where a single resistive passage connects a waste port with a plurality of inlets.

FIG. 2 illustrates diagrammatically in top and side views another embodiment of a fluidic circuit, which uses ring-shaped waste and resistive passages (206 and 208, respectively) to accommodate a greater number of inlets (200) than the embodiment of FIGS. 1A-1D. As above, multiple inlets (200) connect to fluidics node (202) in a surface opposite to that connecting to outlet (204). Fluid flow from an inlet is split in fluidics node (202) so that a portion exits outlet (204) and the remainder exits ring-shaped passage (208), whose width (210) and height (212) are selected to provide fluidic resistance for appropriately splitting the input reagent flow. After sweeping past unselected inlets and passing through resistive passage (208), flow from a selected inlet enters waste ring passage (206) and is directed to waste port (214).

Figure 3A:
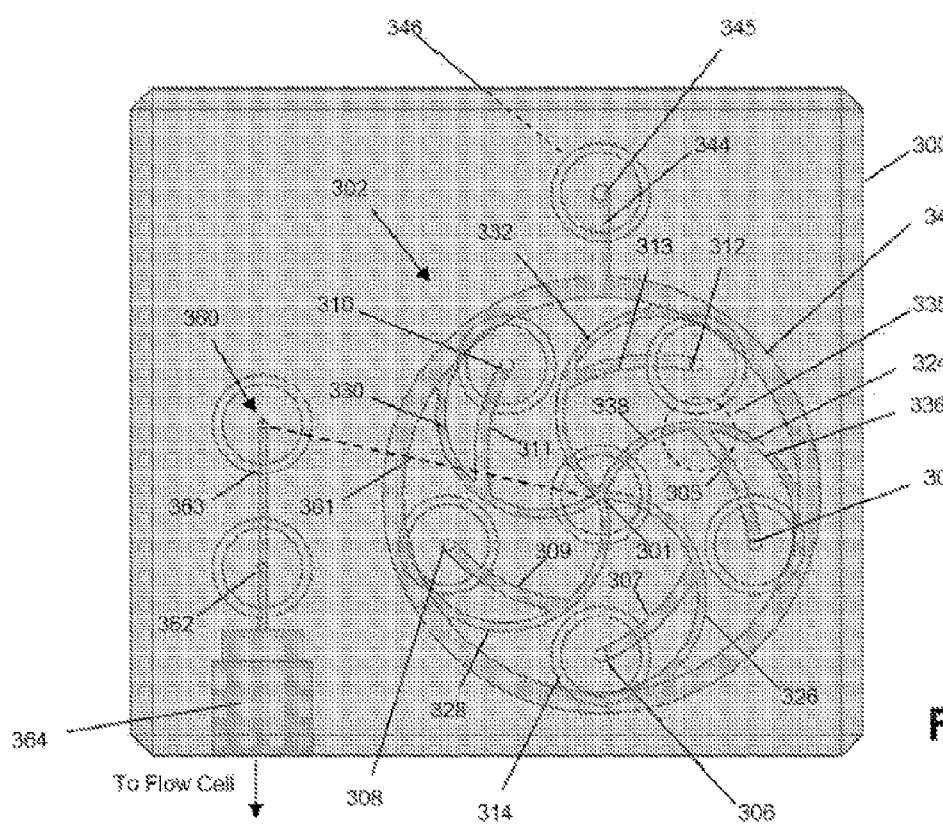
FIGS. 3A-3C illustrate another embodiment of the invention where each of a plurality of inlets is connected to a central fluidics node and a waste port through a planar network of passages.
Figure 3B:
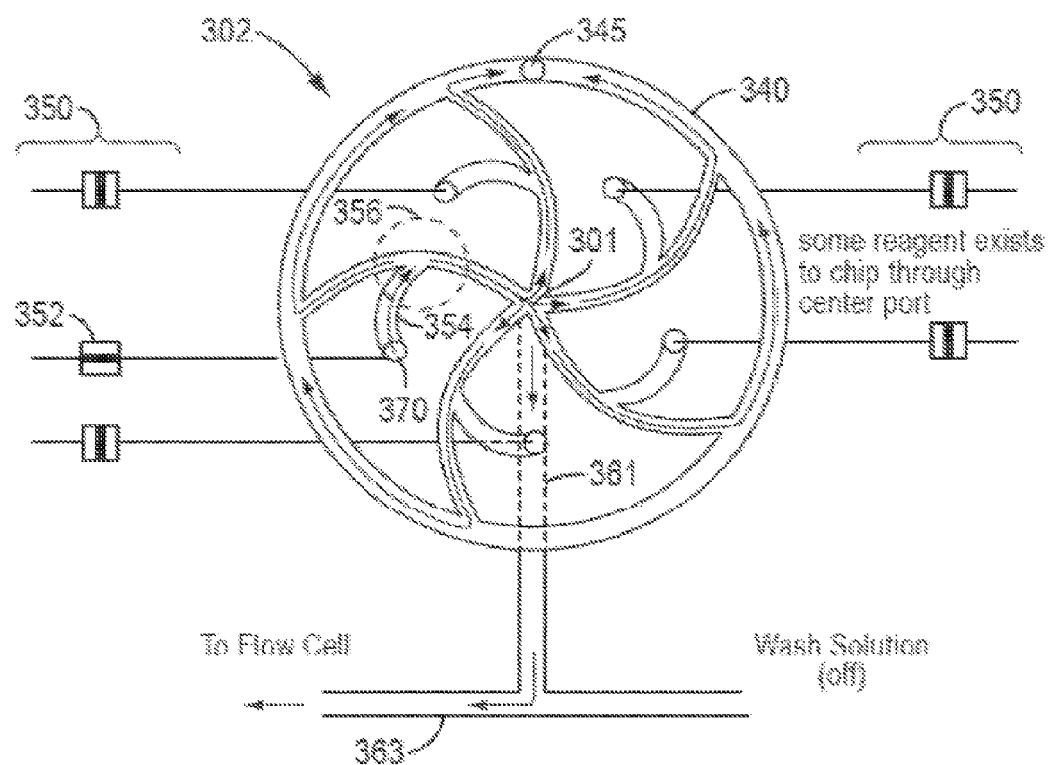
Figure 3C:
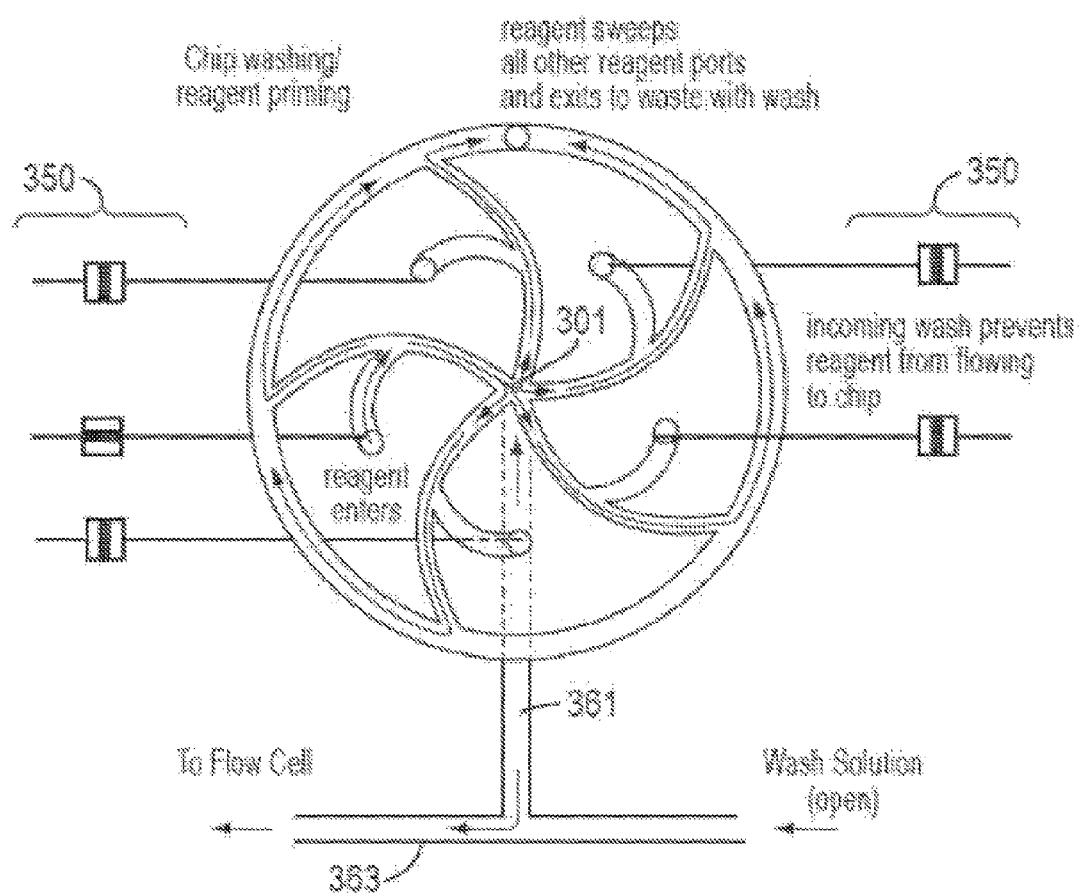

FIGS. 3A-3C diagrammatically illustrate another embodiment of the fluidics circuit of the invention which accommodates five input reagents in a planar circuit structure. FIG. 3A is a top view of a transparent body or housing (300) containing fluidic circuit (302). Housing (300) may be constructed from a variety of materials, including metals, glass, ceramics, plastics, or the like. Transparent materials include polycarbonate, polymethyl methacrylate, and the like. Inlets (or input ports) (304, 306, 308, 310, and 312) are connected by a passage to their respective connector slots (314) located on the bottom side of housing (300) (shown as double circles concentric with the inlets) from which reagents enter fluidic circuit (302). Inlets (304, 306, 308, 310, and 312) are in fluid communication with passages (305, 307, 309, 311, and 313, respectively) which, in turn, are connected to curvilinear passages (324, 326, 328, 330, and 332, respectively). Each curvilinear passage consists of two legs, such as (336) and (338), identified for curvilinear passage (324) at a "T" junction (335), also identified for only curvilinear passage (324). One leg is an inner leg (for example (338)) which connects its respective inlet to node (or multi-use central port) (301) and the other leg is an outer leg (for example (336)) which connects its respective inlet to waste passage (or ring) (340). As mentioned above, the cross-sectional areas and lengths of the inner and outer legs of the curvilinear passages may be selected to achieve the desired balance of flows at the "T" junctions and at node (301). Through passage (344), waste passage (or channel) (340) is in fluid communication with waste port (345) which connects to a waste reservoir (not shown) by connector slot (346) on the bottom side of body (300). Node (301) is in fluid communication with port (360) by passage (361) which in this embodiment is external to body (300) and is illustrated by a dashed line. In other embodiments, passage (361) may be formed in body (300) so that connector slots for node (301) and port (360) are not required. Port (360) is connected by passage (363) to wash solution inlet (362), where a "T" junction is formed, and to connector slot (364) which, in turn, provides a conduit to a flow cell, reaction chamber, or the like. FIGS. 3B and 3C illustrate two of three modes of using the fluidics circuit to distribute fluids to a flow cell. The modes of operation are implemented by valves (350) associated with each of the input reagents and with the wash solution. In a first mode of operation (selected reagent valve open, all other reagent valves closed, wash solution valve closed) (FIG. 3B) a selected reagent is delivered to a flow cell; in a second mode of operation (selected reagent valve open, all other reagent valves closed, wash solution valve open) (FIG. 3C) the fluidic circuit is primed to deliver a selected reagent; and in a third mode of operation (all reagent valves closed wash solution valve open) (not shown), all passages in the fluidics circuit are washed. As mentioned above, associated with each inlet is a valve (350) which can be opened to allow fluid to enter fluidic circuit (302) through its respective inlet (as shown for valve (352)), or closed to prevent fluid from entering circuit (302) (as shown with all valves, except for (352)). In each case, when an inlet's valve is open and the others are closed (including the wash solution valve) as shown for inlet (370) in the FIG. 3B, fluid flows through passage (354) to "T" junction (356) where it is split into two flows, one of which is directed to waste passage (340) and then the waste port (345), and another of which is directed to node (301). From node (301) this second flow again splits into multiple flows, one of which exits node (301) through passage (361) and then to passage (363) and to a flow cell and the other flows to each of the passages connecting node (301) to the other inlets, and then to waste passage (340) and waste port (345). The latter flows pass the other inlets carrying any material diffusing or leaking therefrom and directing it to waste port (345). A sequence of different reagents may be directed to a flow cell by opening the valve of a selected reagent and simultaneously closing the valves of all of the non-selected reagents and the wash solution. In one embodiment, such sequence may be implemented by a sequence of operating modes of the fluidics circuit such as: wash, prime reagent $x_1$, deliver reagent $x_1$, wash, prime reagent $x_2$, deliver reagent $x_2$, wash, and so on. The reagent priming mode of operation is illustrated in FIG. 3C. As in the reagent delivery mode, all reagent inlet valves are closed, except for the valve corresponding to the selected reagent. Unlike the reagent delivery mode, however, the wash solution valve is open and the relative pressure of the selected reagent flow and the wash solution flow is selected so that wash solution flows through passage (361) and into node (301) where it then exits through all the passages leading to waste passage (340), except for the passage leading to the selected reagent inlet.

Figure 4A:
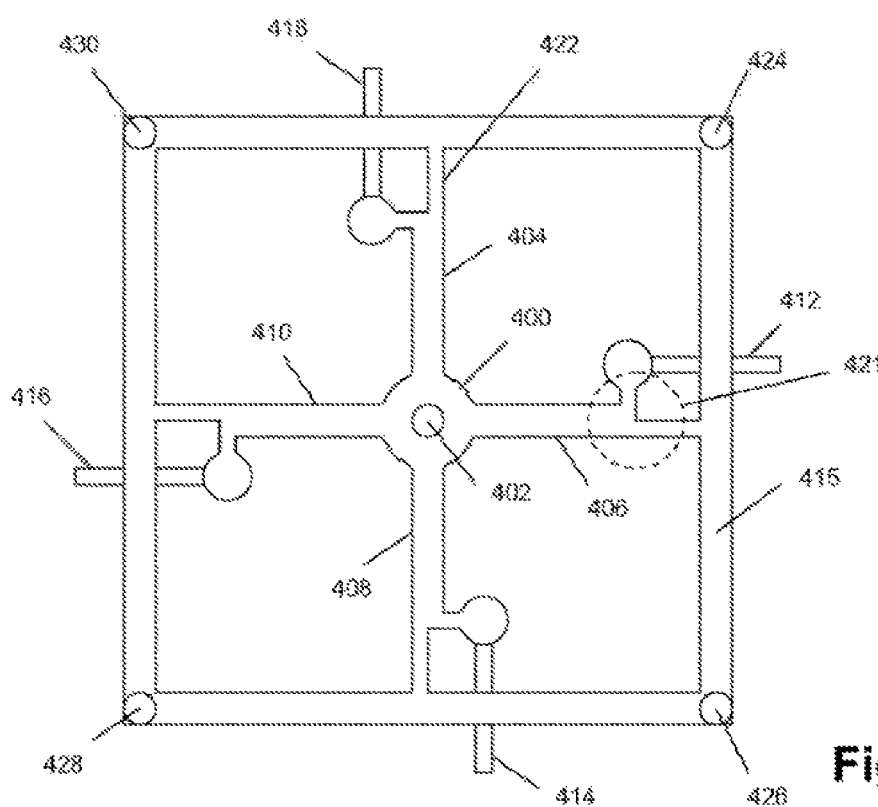
FIGS. 4A-4B illustrate another embodiment having a planar structure that may be duplicated by stacking similar units that are connected through their fluidics nodes and waste passages. thereby enabling the accommodation of more input fluids.
Figure 4B:
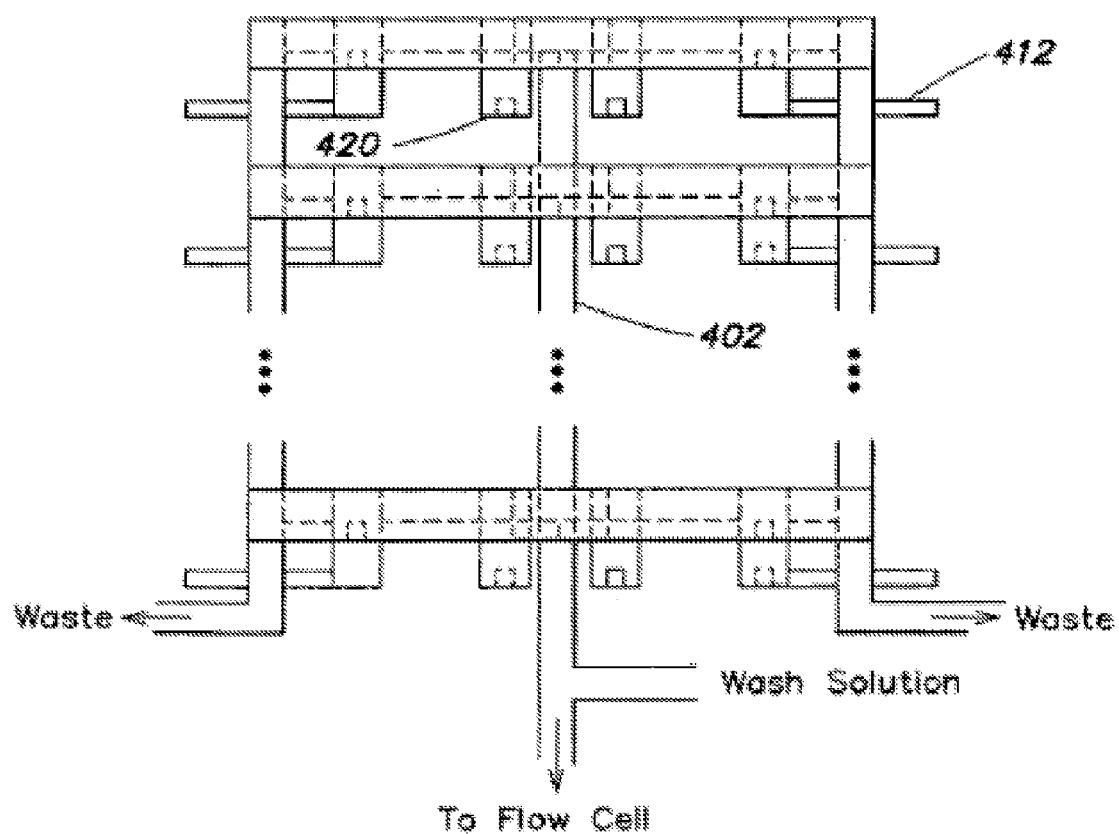

FIGS. 4A-4B diagrammatically illustrates another embodiment of a planar fluidics circuit which accommodates four input reagents and whose design can accommodate further input reagents by stacking of the planar fluidics circuit and connecting their fluidics nodes. The topology and operation of the planar fluidics circuit of FIG. 4A is equivalent to that of FIG. 3A. except that the latter includes an additional inlet and in the former, flows through "T" junctions (as exemplified by (421)) are balanced by selecting different cross-sectional areas of the different legs (one connecting to node (400) and one connecting to waste channel (415)) of each passage (404, 406, 408, and 410), rather than by selecting legs of different length and/or curvature. Inlets (412, 414, 416, and 418) connect to passages (404, 406, 408, and 410, respectively) through "T" junctions, e.g. (421), which, in turn, connect to waste passage or channel (415) and fluidics node (400). Outlet (402) and waste passages (424, 426, 428, and 430) connect a stack of planar fluidic circuits as illustrated in FIG. 4B.

Figure 5:
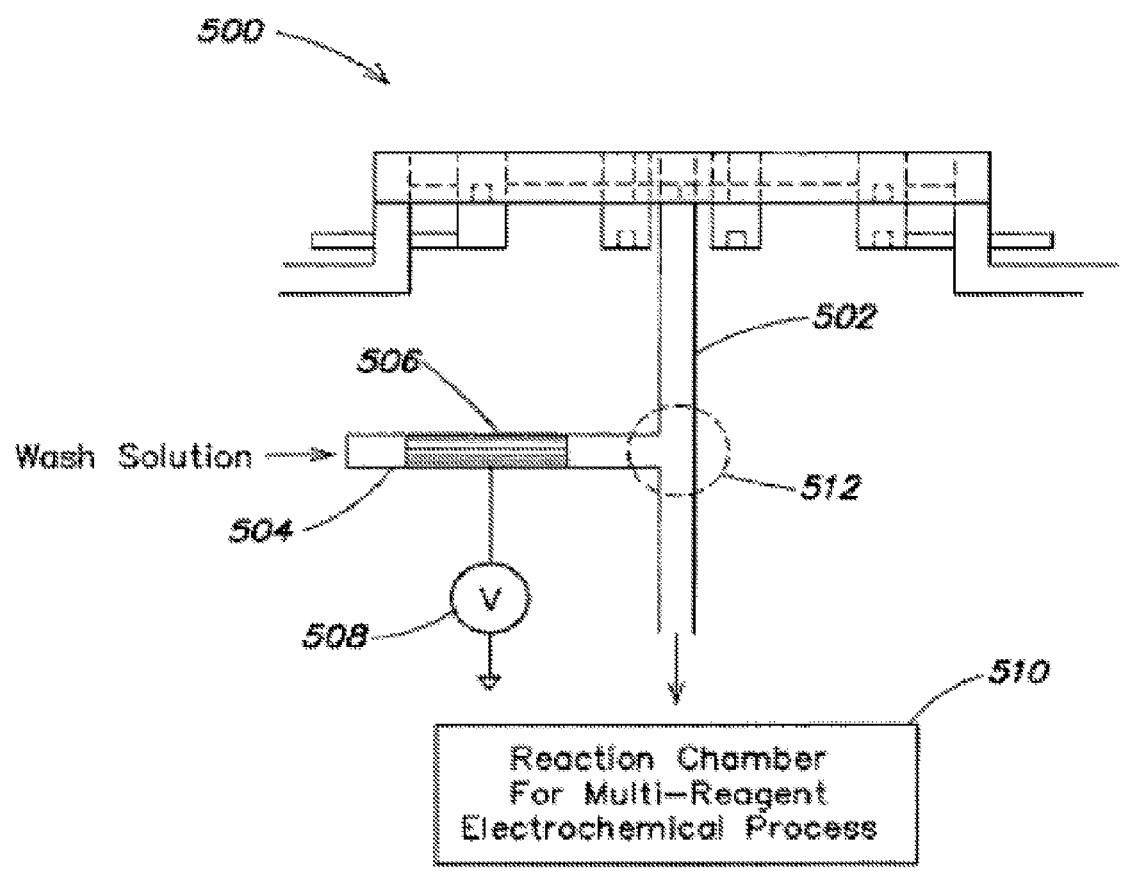
FIG. 5 illustrates how the fluidics circuit of the invention may provide a stable reference electrode for a multi-step electrochemical process.

FIG. 5 diagrammatically illustrates how fluidics circuits of the invention may be used in an electrochemical process requiring multiple reactants, including electrolytes used in such processes, and employing a reference electrode upstream of a reaction chamber. For stable reference voltages, it is desirable that the reference electrode contact no more than a single process reagent. Fluidics circuits of the invention provide a means of delivering a predetermined sequence of electrolytes through a common inlet of a reaction chamber while maintaining (i) uninterrupted fluid communication between the reaction chamber and a reference electrode, and (ii) contact of only a single electrolyte (i.e. a selected electrolyte) with the reference electrode. All of the other reagent or electrolytes (i.e. the unselected electrolytes) never contact the reference electrode. Planar fluidics circuit (500) as described in FIGS. 4A-4B delivers a sequence of different reagents to reaction chamber (510) by passage (502). Flows of wash solution may be directed through passage (504) to "T" junction (512) and back to fluidics circuit (500) and to reaction chamber (510), as described above. A stable reference voltage may be provided to reaction chamber (510) by positioning reference electrode (506) in or adjacent to passage (504). In one embodiment, such reference electrode may be a metal tube forming a section of passage (504), as is illustrated in FIG. 5. Reference electrode (506) is electrically connected to a reference voltage source (508).

In one aspect of the invention, such an apparatus comprises a reaction vessel coupled to an electronic sensor for monitoring products in the reaction vessel: a fluidics system including a fluidics circuit of the invention for sequentially delivering a plurality of different electrolytes including a selected electrolyte to the reaction vessel: and a reference electrode in contact with the selected electrolyte for providing a reference voltage to the electronic sensor, the reference voltage being provided without the reference electrode contacting any unselected electrolytes.

Materials and Methods of Fabrication

As mentioned above, fluidic circuits of the invention may be fabrication by a variety of methods and materials. Factors to be considered in selecting materials include degree of chemical inertness required, operating conditions, e.g. temperature, and the like, volume of reagents to be delivered, whether or not a reference voltage is required, manufacturability, and the like. For small scale fluid deliveries, microfluidic fabrication techniques are well-suited for making fluidics circuits of the invention, and guidance for such techniques is readily available to one of ordinary skill in the art, e.g. Malloy, Plastic Part Design for Injection Molding: An Introduction (Hanser Gardner Publications, 1994); Herold et at, Editors, Lab-on-a-Chip Technology (Vol. 1): Fabrication and Microfluidics (Caister Academic Press, 2009): and the like. For meso-scale and larger scale fluid deliveries conventional milling techniques may be used to fabricate parts that may be assembled into fluidic circuits of the invention. In one aspect, plastics such as polycarbonate, polymethyl methacrylate, and the like, may be used to fabricate fluidics circuits of the invention.

Applications in Electrochemical Processes

Figure 6:
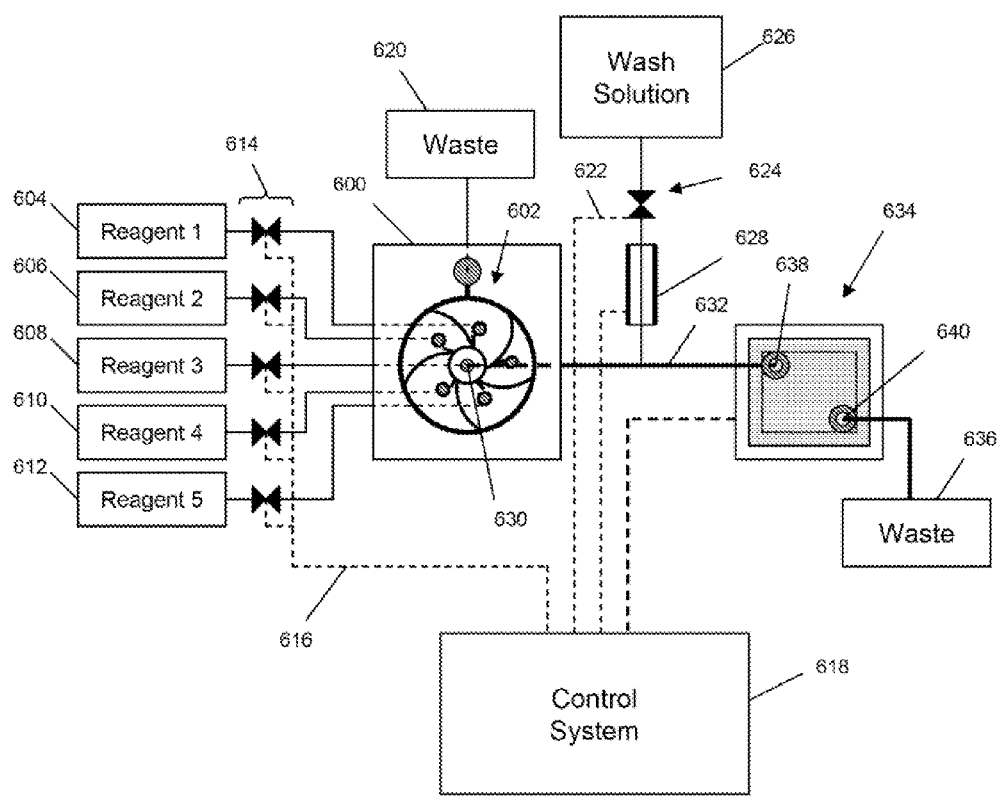
FIG. 6 is a diagrammatic illustration of an exemplary apparatus using a fluidics system of the invention.

Fluidics circuits of the invention are useful in electrochemical processes where multiple reagents are delivered to one or more reactors that are monitored with electronic sensors requiring a reference electrode. Exposure of a reference electrode to multiple reagents can introduce undesirable noise into the signals detected by the electronic sensors. Circumstances where this occurs are in methods and apparatus for carrying out label-free DNA sequencing, and in particular, pH-based DNA sequencing. The concept of label-free DNA sequencing, including pH-based DNA sequencing, has been described in the literature, including the following references that are incorporated by reference: Rothberg et al, U.S. patent publication 2009/0026082; Anderson et al, Sensors and Actuators B Chem., 129: 79-86 (2008); Pourmand et al, Proc. Natl. Acad. Sci., 103: 6466-6470 (2006); and the like. Briefly, in pH-based DNA sequencing, base incorporations are determined by measuring hydrogen ions that are generated as natural byproducts of polymerase catalyzed extension reactions. DNA templates each having a primer and polymerase operably bound are loaded into reaction chambers (such as the microwells disclosed in Rothberg et al, cited above), after which repeated cycles of deoxynucleoside triphosphate (dNTP) addition and washing are carried out. Such templates are typically attached as clonal populations to a solid support, such as a microparticle, bead, or the like, and such clonal populations are loaded into reaction chambers. In each addition step of the cycle, the polymerase extends the primer by incorporating added dNTP only if the next base in the template is the complement of the added dNTP. If there is one complementary base, there is one incorporation, if two, there are two incorporations, if three, there are three incorporations, and so on. With each such incorporation there is a hydrogen ion released, and collectively a population of templates releasing hydrogen ions causing very slight changes the local pH of the reaction chamber which is detected by an electronic sensor. FIG. 6 diagrammatically illustrates an apparatus employing a fluidics circuit of the invention for carrying out pH-based nucleic acid sequencing in accordance with Rothberg et al (cited above). Each electronic sensor of the apparatus generates an output signal that depends on the value of a reference voltage. The fluid circuit of the apparatus permit multiple reagents to be delivered to the reaction chambers with no more than one of them contacting the reference electrode, thereby removing a source of noise from the output signals generated by the sensors. In FIG. 6, housing (600) containing fluidics circuit (602) is connected by inlets to reagent reservoirs (604, 606, 608, 610, and 612), to waste reservoir (620) and to flow cell (634) by passage (632) that connects fluidics node (630) to inlet (638) of flow cell (634). Reagents from reservoirs (604, 606, 608, 610, and 612) may be driven to fluidic circuit (602) by a variety of methods including pressure, pumps, such as syringe pumps, gravity feed, and the like, and are selected by control of valves (614), as described above. The foregoing comprises a fluidics system of the instrument of FIG. 6. Control system (618) includes controllers for valves (614) that generate signals for opening and closing via electrical connection (616). Control system (618) also includes controllers for other components of the system, such as wash solution valve (624) connected thereto by (622), and reference electrode (628). Control system (618) may also include control and data acquisition functions for flow cell (634). In one mode of operation, fluidic circuit (602) delivers a sequence of selected reagents (1, 2, 3, 4, or 5) to flow cell (634) under programmed control of control system (618), such that in between selected reagent flows fluidics circuit (602) is primed and washed, and flow cell (634) is washed. Fluids entering flow cell (634) exit through outlet (640) and are deposited in waste container (636). Throughout such an operation, the reactions and/or measurements taking place in flow cell (634) have a stable reference voltage because reference electrode (628) has a continuous, i.e. uninterrupted, electrolyte pathway with flow cell (634), but is in physical contact with only the wash solution.

Figure 7:
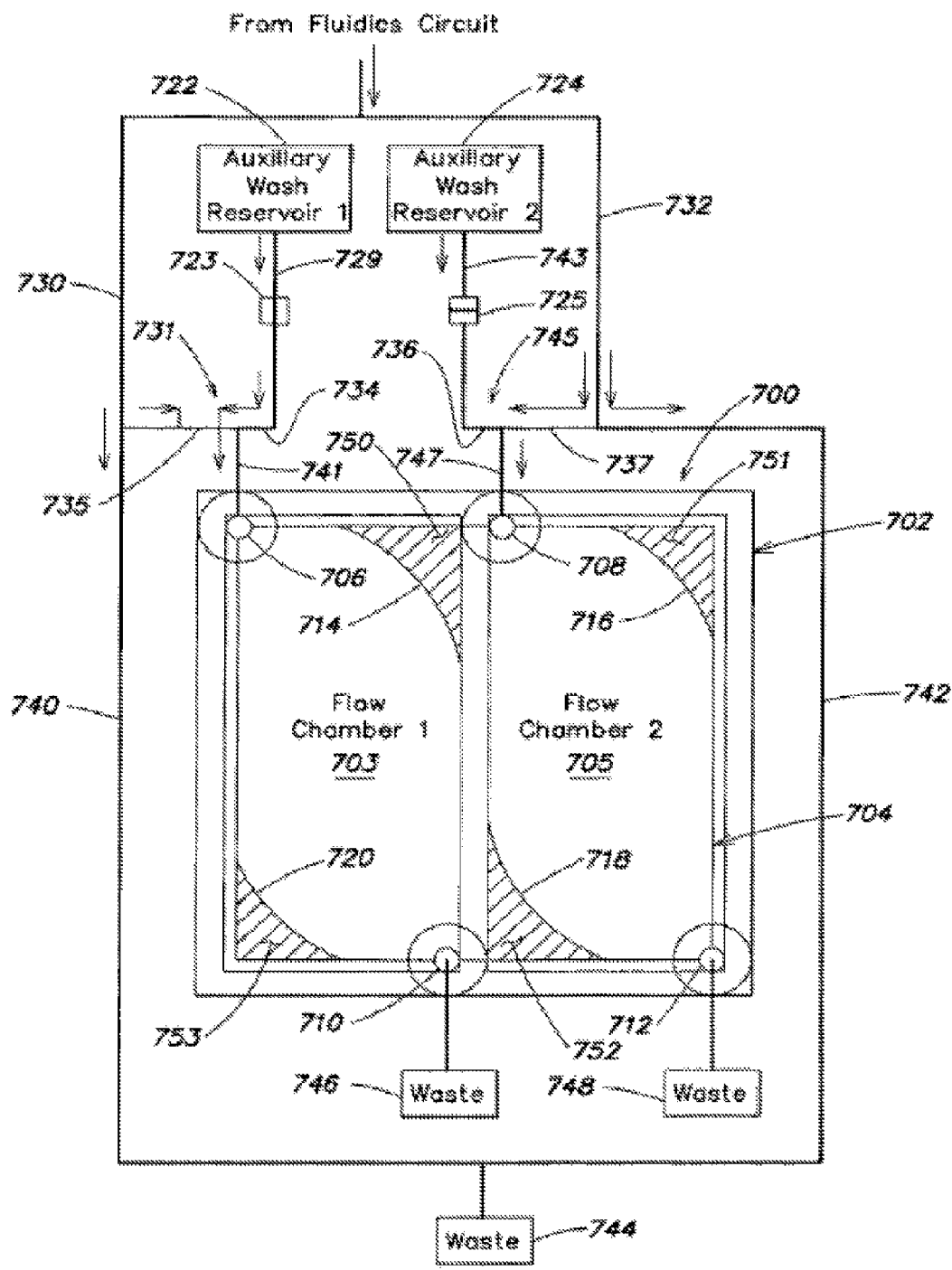
FIG. 7 illustrates an embodiment providing separate wash control in a dual-flow chamber flow cell that provides an uninterrupted fluid path between a reference electrode and both chambers of the flow cell.

FIG. 7 illustrates how the fluidics circuit design concepts may be used to make a plurality of separate flow chambers using a single large flow cell and sensor array, wherein reagent access to each flow chamber is separately controlled while still maintaining uninterrupted fluid pathways to the reference electrode for all sensors in all the flow chambers. FIG. 7 is a top view of flow cell (700) that has fluidics interface member (702) mounted on and is sealingly attached to a housing (not shown) that holds sensor array (704) and defines two flow chambers (703) and (705), each having separate inlets (706 and 708, respectively) and separate diagonally opposed outlets (710 and 712, respectively) that are each connected to a common source of reagents from a fluidics circuit via passages 730 and 735 for flow chamber 1 and 732 and 737 for flow chamber 2, and to separate auxiliary wash reservoirs: 722 for flow chamber 1 and 724 for flow chamber 2. Interior walls (714, 716,718 and 720) formed by attachment of fluidics interface member (702) to the chip housing defines the flow paths through flow chambers (703) and (705) and exclude opposing corner regions (750, 751, 752, and 753) from having contact with reagents passing through the flow chambers.

When valve (723) is open, wash solution from the auxiliary wash reservoir 1 (722) passes through passage (729), through valve (723), to passage (734), and to junction (731), where the flow splits between passage (735) and passage (741). As with the design of the fluidics circuits described above, the lengths and cross-sections of passages (735) and (734), and the driving forces of the wash solution and reagent are selected so that when valve (723) is open (as shown) solely wash solution enters flow chamber 1 and reagent from the fluidics circuit is directed solely to waste reservoir (744). When valve (723) is closed, then no wash solution moves in passage (729) and there is no barrier to the flow of reagent from passage (730), to passage (735), to passage (741), and to flow chamber 1. Likewise, when valve (725) is open, wash solution from the auxiliary wash reservoir 2 (724) passes through passage (743), through valve (725), to passage (736), and to junction (745), where the flow splits between passage (737) and passage (747). As above, the lengths and cross-sections of passages (736) and (737), and the driving forces of the wash solution and reagent are selected so that when valve (725) is open solely wash solution enters flow chamber 2 and reagent from the fluidics circuit is directed solely to waste reservoir (744). When valve (725) is closed (as shown), then no wash solution moves in passage (743) and there is no barrier to the flow of reagent from passage (732), to passage (737), to passage (747), and to flow chamber 2.

While the present invention has been described with reference to several particular example embodiments, those skilled in the art will recognize that many changes may be made thereto without departing from the spirit and scope of the present invention. The present invention is applicable to a variety of sensor implementations and other subject matter, in addition to those discussed above.

DEFINITIONS

"Microfluidics device" means an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, detection systems, data collection and/or integration systems, and the like. Microfluidics devices may further include valves, pumps, and specialized functional coatings on interior walls, e.g. to prevent adsorption of sample components or reactants, facilitate reagent movement by electroosmosis, or the like. Such devices are usually fabricated in or as a solid substrate, which may be glass, plastic, or other solid polymeric materials, and typically have a planar format for ease of detecting and monitoring sample and reagent movement, especially via optical or electrochemical methods. Features of a microfluidic device usually have cross-sectional dimensions of less than a few hundred square micrometers and passages typically have capillary dimensions, e.g. having maximal cross-sectional dimensions of from about 500 μm to about 0.1 μm. Microfluidics devices typically have volume capacities in the range of from 1 μm to a few nL, e.g. 10-100 nL. The fabrication and operation of microfluidics devices are well-known in the art as exemplified by the following references that are incorporated by reference: Ramsey, U.S. Pat. Nos. 6,001,229; 5,858,195; 6,010,607; and 6,033,546; Soane et al. U.S. Pat. Nos. 5,126,022 and 6,054,034; Nelson et al, U.S. Pat. No. 6,613,525; Maher et al, U.S. Pat. No. 6,399,952: Ricco et al, International patent publication WO 02/24322: Bjornson et al, International patent publication WO 99/19717; Wilding et al, U.S. Pat. Nos. 5,587,128; 5,498,392; Sia et at, Electrophoresis, 24: 3563-3576 (2003); Unger et al. Science, 288: 113-116 (2000); Enzelberger et al, U.S. Pat. No. 6,960,437.

What is claimed is:

1. A fluidic device comprising:
a node having a fluid outlet;
a plurality of fluid inlets, each fluid inlet of the plurality of fluid inlets uniquely associated with a respective reagent of a plurality of reagents;
at least one waste port;
a plurality of passages, each passage of the plurality of passages providing a distinct fluid pathway between the node and the at least one waste port, each passage of the plurality of passages including a junction to a respective inlet passage providing fluid communication between the each passage and a respective fluid inlet of the plurality of fluid inlets;
an outlet passage in fluid communication with the node through the fluid outlet; and
a wash fluid inlet in fluid communication with the outlet passage.

2. The fluidic device of claim 1, wherein each reagent of the plurality of reagents is stored in a respective reservoir.

3. The fluidic device of claim 1, further comprising a reference electrode in electrical communication with the wash fluid inlet.

4. The fluidic device of claim 1, wherein the wash fluid inlet includes a wash fluid inlet passage connected to the outlet passage, the reference electrode disposed in the wash fluid inlet passage.

5. The fluidic device of claim 1, wherein the outlet passage is in fluid communication with a flow cell.

6. The fluidic device of claim 5, further comprising a reference electrode having a continuous electrolyte pathway from a wash fluid inlet passage through the outlet passage to the flow cell.

7. The fluidic device of claim 1, wherein each distinct fluid pathway is free of impermeable barriers.

8. The fluidic device of claim 1, wherein each passage includes an inner leg extending from the junction to the node and an outer leg extending from the junction toward the at least one waste port.

9. The fluidic device of claim 1, wherein the second segment is connected to a waste passage in fluid communication with the waste port.

10. The fluidic device of claim 1, wherein the second segment has greater flow resistance than the first segment.

* * * * *